United States Patent [19]

Iguchi et al.

[11] Patent Number: 4,800,160

[45] Date of Patent: Jan. 24, 1989

[54] PROCESS AND APPARATUS FOR PRODUCING IMMOBILIZED ENZYME GRANULES

[75] Inventors: Seiya Iguchi, Tokyo; Takeshi Noguchi, Yokohama; Hiroshi Kimura, Kamakura; Masayo Aihara, Yokohama, all of Japan

[73] Assignee: Mitsui Toatsu Chemical, Incorporated, Tokyo, Japan

[21] Appl. No.: 889,764

[22] Filed: Jul. 28, 1986

[30] Foreign Application Priority Data

Aug. 6, 1985 [JP] Japan ................................ 60-171786

[51] Int. Cl.$^4$ ..................... C12N 11/02; C12N 11/10; C12N 11/04; C12M 1/40
[52] U.S. Cl. .................................. 435/177; 435/178; 435/182; 435/288
[58] Field of Search ............... 435/174, 177, 178, 182, 435/288; 244/4, 8, 13, 14

[56] References Cited

U.S. PATENT DOCUMENTS

| | | | |
|---|---|---|---|
| 3,499,745 | 3/1970 | Plumat | 264/8 X |
| 4,138,292 | 2/1979 | Chibata et al. | 435/178 |
| 4,218,409 | 8/1980 | Dannelly | 264/4 |
| 4,386,895 | 6/1983 | Sodickson | 264/4 X |
| 4,391,909 | 7/1983 | Lim | 435/182 X |
| 4,613,076 | 9/1986 | Dietz et al. | 264/8 X |

FOREIGN PATENT DOCUMENTS 1573181 7/1980 United Kingdom .

*Primary Examiner*—David M. Naff
*Attorney, Agent, or Firm*—Nixon & Vanderhye

[57] ABSTRACT

Enzyme-containing granules are produced by forming drops of a gellable enzyme-containing liquid with a rotating disc and bringing the drops in contact with a gelling solution. The disc is preferably contained in a column, and the gelling solution flows down walls of the column to a reservoir in a lower legion of the column. Drops of the enzyme-containing liquid from the rotating disc contact the gelling solution while flowing down the walls and are carried to the reservoir. Preferably, the enzyme-containing liquid is an aqueous alginate solution containing the enzyme and the gelling solution is an aqueous calcium chloride solution.

9 Claims, 2 Drawing Sheets

PROCESS AND APPARATUS FOR PRODUCING IMMOBILIZED ENZYME GRANULES

BACKGROUND OF THE INVENTION

(1) Field of the Invention:

This invention relates to a process for preparing immobilized enzymes in a short period of time and in large amounts and to an apparatus useful for carrying out the process. This invention may advantageously be applied to the preparation of immobilized enzymes used in the operation of a bioreactor.

(2) Description of the Prior Art:

A variety of techniques for preparing immobilized enzymes to be used in a bioreactor are known, for example, it is known that liquid drops or droplets may be produced by forcing an enzyme-containing liquid from the tip of a small nozzle under a given pressure using a compressed gas, in addition to the entrapping immobilization method using carrageenan as disclosed by U.S. Pat. No. 4,138,292 to Chibata et al.

In these methods, a mixture of a sodium alginate solution or an aqueous carrageenan solution with a microorganism is dropped in an aqueous solution of a gelling agent such as calcium chloride to produce entrapped microorganism gel granules. These conventional methods are however still disadvantageous in the granulation ability when large quantities of the gel granules are desired to be produced. They also involve the problem that suspended drops are formed on the jet of the nozzle, thereby requiring occasional wiping of the nozzle tip. Thus, none of these methods has been regarded as appropriate for treating a large amount of microorganism in a short period of time.

SUMMARY OF THE INVENTION

It is an object of the present invention to provide a process for preparing a large quantity of an immobilized enzyme in a short period of time and an apparatus for effecting that process. The present invention provides a novel process for preparing gel granules of an immobilized microorganism or immobilized enzyme in large amounts and an apparatus therefor. In accordance with the present invention, a large amount of the immobilized gel granules can be produced vary rapidly. As a result, this short period of time in the immobilization operation makes it feasible to minimize the deactivation of the enzymatic activity during the operation.

The outline of the present invention relates to a process which comprises mixing a crude enzyme extract or a microorganism with a carrier solution thereof, feeding the mixed liquid, i.e., the enzymecontaining liquid, to a rotating disc so as to release liquid drops or droplets from the periphery of the disc, and bringing the liquid drops or droplets into contact with an aqueous solution of a gelling agent or an solidifying solution, thereby preparing an immobilized enzyme, and an apparatus for effecting the process, i.e., an apparatus provided with a vessel for preparing, storing and supplying the enzymecontaining liquid, a rotating disc for releasing the liquid from its periphery as liquid drops or droplets by centrifugal force and a vessel for bringing the released liquid drops or droplets into contact with a gelling solution, characterized in that the rotating disc used in said apparatus is a rotating disc with saw-toothed cuts at its periphery, and in that a plurality of rotating discs are provided in this apparatus.

Figure 1:
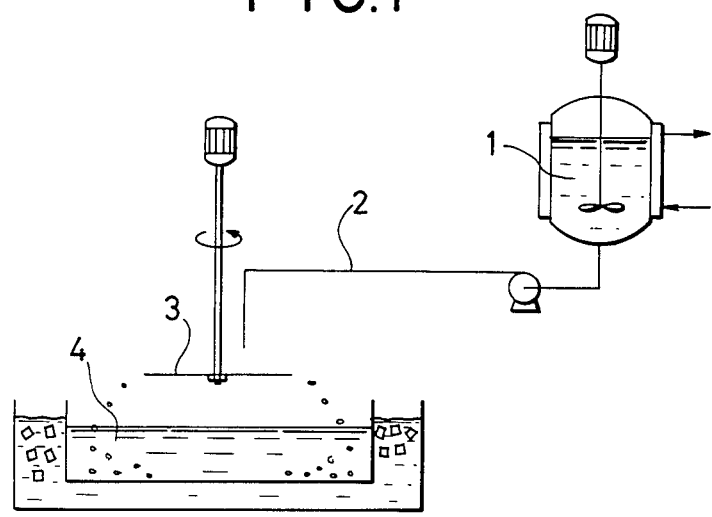
FIG. 1 illustrates an apparatus for effecting the process of the present invention.

In each drawing, reference numerals 1, 2, 3, 4 and 5 represent an enzyme-containing liquid, a liquid feed pipe, a disc, a solidifying solution and a wetted wall column, respectively.

DETAILED DESCRIPTION OF THE INVENTION

In FIG. 1, a disc 3 fixed to the rotating axis of a motor is provided over a sufficiently large vessel containing a gelling solution 4. The vessel containing the gelling solution is cooled in a cold water bath generally kept cold with ice. Separately, an enzyme-containing liquid, or a mixed liquid of an enzyme or a microorganism holding an enzyme with a carrier solution, is stirred and prepared in a liquid feed tank. It is preferable to cool the liquid feed tank by means of, for example, a jacket in order to maintain the enzymatic activity of the feed liquid. The enzyme-containing liquid is allowed to flow down onto a rotating disc or preferably onto the vicinity of the center thereof through a liquid feed pipe 2 by means of a pump. Then, the enzyme-containing liquid on the rotating disc is caused to flow in radial directions to the periphery by centrifugal force. The liquid finally flies from the periphery and falls into the gelling solution in which gel granules are formed by a gellation reaction.

Figure 2:
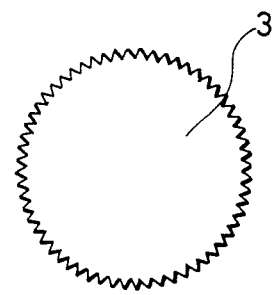
FIG. 2 illustrates a disc having saw-toothed cuts at its periphery.

FIG. 2 illustrates a rotating disc with saw-toothed cuts at the periphery thereof for use in the process and apparatus of the present invention.

Figure 3:
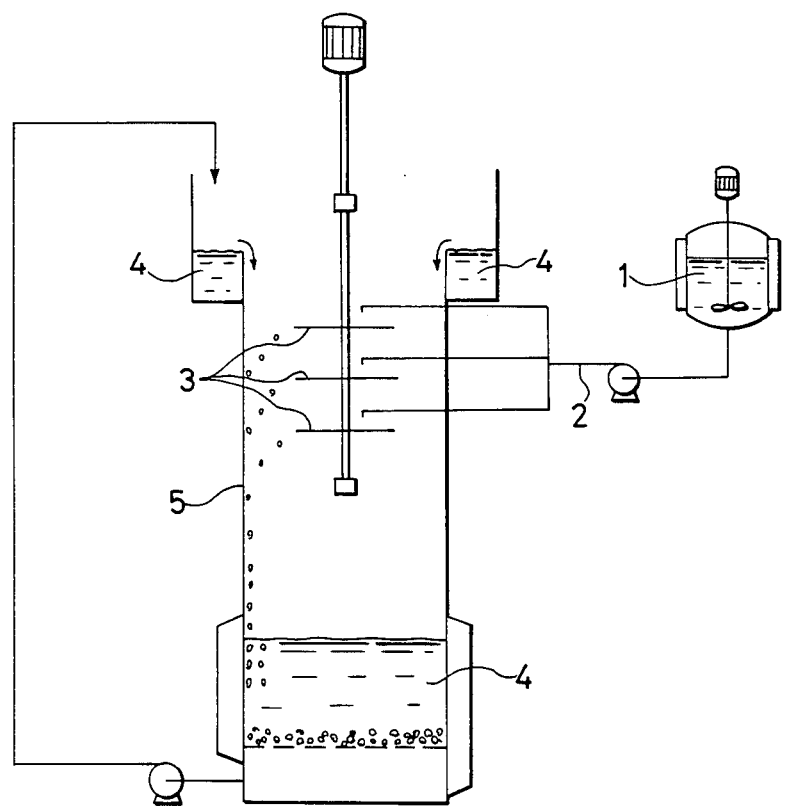
FIG. 3 illustrates an apparatus which uses a plurality of discs and is of the wetted wall type.

FIGS. 1 and 2 show the fundamental principle of the process and apparatus of the present invention, while FIG. 3 illustrates an exemplary apparatus for the mass production of the immobilized granules in accordance with the present invention, in which apparatus a plurality of rotating disc are used. A plurality of rotating discs are fixed to the rotating axis of a motor, each disc being attended by a liquid feed unit for feeding the enzyme-containing liquid to the disc.

The gelling solution may be held in a vessel set under the disc as shown in FIG. 1 or may be allowed to flow down so as to form a wetted wall 5 around the disc like the wetted wall column as shown in FIG. 3.

In FIG. 3, the gelling solution caused to flow down to the bottom of the column is separated from the formed granules and circulated to the top of the wetted wall column so that it may be repeatedly used as a gelling solution. Some fresh gelling solution may also be added. This scheme is particularly effective in producing an immobilized microoragnism gel in large amounts.

As the microorganism may be used common yeasts such Candida and Saccharomyces and common bacteria such as Pseudomonas, *Escherichia coli,* Norcadia, Gluconobacter and Zymomonas. No particular limitations are imposed on the species. Also, no particular restrictions are placed on the variety of enzymes.

As the carrier of an enzyme or microorganism for the immobilization, an alginate solution, and carrageenan, among others, are well known and widely applied. It is a matter of course that no limitations are vested on their kind in the present invention.

According to the present invention, each immobilized microorganism granule formed has an average size of approximately 0.5-6 mm. Proper selection of the diameter and revolution of the rotating disc makes it possible to produce granules of desired sizes. Generally, granules of 2-3 mm in size are widely used.

As the gelling solution, an aqueous solution of calcium chloride is generally used.

In accordance with the present invention, the immobilized enzyme granule is not always of a perfect sphere but frequently of a drop or droplet. The aspect ratio of granules is in the order of 1.6-3.0, which causes no particular inconvenience in practical use.

It is generally preferable that the gel formed from the liquid fallen into the gelling solution after flying from the rotating disc be aged by being brought into contact with the gelling solution for a certain period of time so that the gellation is further proceeded.

The present invention is described by way of the following examples. It should however be understood that the present invention is not limited to or by these examples.

EXAMPLE 1

The following is the case wherein an immobilized microorganism is prepared using the apparatus shown in FIG. 1 and the rotating disc illustrated in FIG. 2.

*Escherichia coli* was cultivated in a culture medium containing glucose and collected by using a centrifuge. The thus-collected wet microorganism was mixed with an equal amount by weight of an isotonic sodium chloride solution and further with four times as much of a 6 wt. % aqueous sodium alginate solution, thereby preparing a suspension of the microorganism.

The resulting suspension was charged in a vessel and kept at about 20° C. Separately, a 0.5 mol per liter aqueous calcium chloride solution was used as a gelling solution.

The suspension was fed onto a rotating disc by a pump and then allowed to fall into the gelling solution cooled at about 10° C. as drops of droplets, thereby aging them in the gelling solution for about one hour. After the aging, the granules were taken out of the gelling solution and their granular sizes were measured. The results are shown in Table 1. The diameter of the disc used in the experiment was 150 mm, the number of teeth was 70, and the tooth depth was 9 mm.

TABLE 1

Results of Preparation Test of Immobilized Microorganism Using Rotating Disc

| Liquid Feed Rate g/H | Disc Revolution rpm | Average Granular Size mm | Aspect Ratio of Granules — |
|---|---|---|---|
| 250 | 155 | 3.9 | 1.8 |
|  | 177 | 3.4 | 2.0 |
|  | 236 | 3.3 | 2.5 |
|  | 311 | 2.5 | 2.3 |
|  | 430 | 1.6 | 1.7 |
| 1,883 | 150 | 6.4 | 2.4 |
|  | 300 | 4.8 | 2.8 |
|  | 390 | 2.4 | 1.7 |
|  | 450 | 2.0 | 2.2 |
| 3,320 | 250 | 4.9 | 2.8 |
|  | 320 | 4.1 | 2.7 |
|  | 390 | 3.7 | 3.1 |
|  | 433 | 2.5 | 2.3 |

EXAMPLE 2

An immobilized microorganism was prepared using the apparatus employed in Example 1 except that a disc with no saw-toothed cuts at its periphery was used. When the liquid feed rate was low, results similar to those of Example 1 were obtained.

EXAMPLE 3

The apparatus illustrated in FIG. 3 was equipped with three discs similar to that used in Example 1 to prepare an immobilized microorganism.

The experiment was conducted at a liquid feed rate of 10 kg/H and a disc revolution of 420 rpm, using a 0.5 mol per liter aqueous calcium chloride solution as a gelling solution. After 30 minutes of operation, an immobilized microorganism having an average granular size of 2.6 mm was obtained in an amount of 4.2 kg.

What is claimed is:

1. A process for the production of immobilized enzyme granules from droplets of an enzyme-containing liquid comprising the steps of:
    (a) providing a substantially vertical column having therein at least one rotating disc surrounded by walls of the column and containing in a lower region thereof a reservoir of a gelling solution for gelling an enzyme-containing liquid;
    (b) providing a supply of the gelling solution at an upper region of the column and allowing the gelling solution to flow downwardly as a layer on the column walls to the gelling solution reservoir;
    (c) forming droplets of an enzyme-containing liquid by supplying the enzyme-containing liquid to said rotating disc disposed within the column and then allowing the supplied enzyme-containing liquid to be centrifugally radially expelled from the rotating disc towards the flowing layer of the gelling solution on the walls of the column, wherein the formed droplets come into contact with the flowing layer and are carried therewith to the gelling solution reservoir; and
    (d) gelling the formed droplets in the gelling solution reservoir to form the immobilized enzyme granules therefrom.

2. A process as in claim 1, further comprising the step of recirculating a portion of the gelling solution from the reservoir to the upper region of the column, and then allowing the recirculated portion to form the flowing layer on the column walls.

3. A process as in claim 2, wherein said step of recirculating the gelling solution portion includes separating the formed immobilized enzyme granules from the recirculated gelling solution portion.

4. A process as in claim 3, wherein said step of recirculating the gelling solution portion also includes supplying additional gelling solution.

5. A process as in claim 1, which further comprises cooling the gelling solution reservoir.

6. Apparatus for the production of immobilized enzyme granules comprising:
    a substantially vertical column having therein at least one rotatable disc surrounded by walls of the column and having a reservoir for containing a gelling solution in a lower region thereof,
    means for supplying an enzyme-containing liquid to said at least one rotatable disc;
    means for supplying a gelling solution for gelling said enzymecontaining liquid to an upper region of the column to form a layer of gelling solution flowing down the walls of the column; and means for rotating said at least one disc to cause enzyme-containing liquid supplied thereto to be centrifugally radially expelled from the disc towards the column walls in the form of liquid enzyme-containing droplets; such that the droplets come into contact with gelling solution flowing down the walls of the column and are carried to the reservoir.

7. Apparatus as in claim 6, which further comprises means for recirculating at least a portion of said gelling solution from the reservoir to the upper region of the column to allow the recirculated gelling solution portion to form a flowing layer on the column wall.

8. Apparatus as in claim 6, further comprising means for cooling the gelling solution reservoir.

9. Apparatus as in claim 6, which includes a plurality of said rotatable discs coaxially separated one from another within said column, said supply means supplying said enzyme-containing liquid to each of said discs.

* * * * *